United States Patent
Sullivan et al.

(10) Patent No.: US 6,984,207 B1
(45) Date of Patent: Jan. 10, 2006

(54) PASSIVE PHYSIOLOGICAL MONITORING (P2M) SYSTEM

(75) Inventors: Patrick K. Sullivan, Honolulu, HI (US); Ken C. K. Cheung, Honolulu, HI (US); Christopher J. Sullivan, Honolulu, HI (US); Paul Pernambuco-Wise, Honolulu, HI (US)

(73) Assignee: Hoana Medical, Inc., Honolulu, HI (US)

( * ) Notice: Subject to any disclaimer, the term of this patent is extended or adjusted under 35 U.S.C. 154(b) by 0 days.

(21) Appl. No.: 09/662,006

(22) Filed: Sep. 14, 2000

Related U.S. Application Data

(60) Provisional application No. 60/153,679, filed on Sep. 14, 1999.

(51) Int. Cl.
*A61B 5/00* (2006.01)
(52) U.S. Cl. .................. 600/301; 600/300; 600/481
(58) Field of Classification Search ............... 600/529, 600/534, 485, 500–507, 481, 300, 301, 586, 600/595
See application file for complete search history.

(56) References Cited

U.S. PATENT DOCUMENTS

| | | | |
|---|---|---|---|
| 3,926,177 A | 12/1975 | Hardway, Jr. et al. | |
| 3,996,922 A | 12/1976 | Basham | |
| 4,033,332 A | 7/1977 | Hardway, Jr. et al. | |
| 4,245,648 A | * | 1/1981 | Trimmer et al. ............ 600/493 |
| 4,320,766 A | 3/1982 | Alihanka et al. | |
| 4,381,788 A | 5/1983 | Douglas | |
| 4,403,215 A | 9/1983 | Hofmann et al. | |
| 4,429,699 A | 2/1984 | Hatschek | |

(Continued)

FOREIGN PATENT DOCUMENTS

GB  2138144 A  10/1984

(Continued)

OTHER PUBLICATIONS

"Bedding", Webster's Revised Unabridged Dictionary, 1998, http://dictionary.reference.com/search?q=bedding.*

(Continued)

*Primary Examiner*—Robert L. Nasser
*Assistant Examiner*—Patricia Mallari
(74) *Attorney, Agent, or Firm*—Fulwider Patton Lee & Utecht, LLP

(57) ABSTRACT

Passive Physiological monitoring apparatus and method have a sensor for sensing physiological phenomenon. A converter converts sensed data into electrical signals and a computer receives and computes the signals, and outputs computed data for real-time interactive display. The sensor is a piezoelectric film of polyvinylidene fluoride. A bandpass filter filters out noise and isolates the signals to reflect data from the body. A pre-amplifier amplifies signals. Signals detected include mechanical, thermal and acoustic signatures reflecting cardiac output, cardiac function, internal bleeding, respiratory, pulse, apnea, and temperature. A pad may incorporate the PVDF film and may be fluid-filled. The film converts mechanical energy into analog voltage signals. Analog signals are fed through the band-pass filter and the amplifier. A converter converts the analog signals to digital signals. A Fourier transform routine is used to transform into the frequency domain. A microcomputer is used for recording, analyzing and displaying data for on-line assessment and for providing realtime response. A radio-frequency filter may be connected to a cable and the film for transferring signals from the film through the cable. The sensor may be an array provided in a MEDEVAC litter or other device for measuring acoustic and hydraulic signals from the body of a patient for field monitoring, hospital monitoring, transport monitoring, home, remote monitoring.

33 Claims, 8 Drawing Sheets

Heart Rate & Respiration

U.S. PATENT DOCUMENTS

| | | | |
|---|---|---|---|
| 4,438,771 A | 3/1984 | Friesen et al. | |
| 4,446,869 A | 5/1984 | Knodle | |
| 4,459,991 A | 7/1984 | Hatschek | |
| 4,474,185 A | 10/1984 | Diamond | |
| 4,475,557 A | 10/1984 | Hatschek et al. | |
| 4,494,553 A | 1/1985 | Sciarra et al. | |
| 4,513,748 A | 4/1985 | Nowogrodzki et al. | |
| 4,537,200 A * | 8/1985 | Widrow | 600/509 |
| RE32,180 E | 6/1986 | Lewiner et al. | |
| 4,595,016 A | 6/1986 | Fertig et al. | |
| 4,657,026 A | 4/1987 | Tagg | |
| 4,660,564 A * | 4/1987 | Benthin et al. | 600/449 |
| 4,686,999 A * | 8/1987 | Snyder et al. | 600/529 |
| 4,757,825 A | 7/1988 | Diamond | |
| 4,773,422 A * | 9/1988 | Isaacson et al. | 600/326 |
| 4,862,144 A * | 8/1989 | Tao | 340/573.1 |
| 4,889,131 A | 12/1989 | Salem et al. | |
| 4,989,611 A * | 2/1991 | Zanetti et al. | 600/508 |
| 5,002,060 A | 3/1991 | Nedivi | |
| 5,148,002 A | 9/1992 | Kuo et al. | 219/211 |
| 5,241,964 A * | 9/1993 | McQuilkin | 600/485 |
| 5,309,916 A * | 5/1994 | Hatschek | 600/485 |
| 5,448,996 A | 9/1995 | Bellin et al. | |
| 5,479,932 A * | 1/1996 | Higgins et al. | 600/529 |
| 5,515,865 A * | 5/1996 | Scanlon | 600/534 |
| 5,544,651 A | 8/1996 | Wilk | 128/633 |
| 5,620,003 A * | 4/1997 | Sepponen | 600/527 |
| 5,684,460 A * | 11/1997 | Scanlon | 340/573.1 |
| 5,724,025 A * | 3/1998 | Tavori | 340/573.1 |
| 5,807,267 A * | 9/1998 | Bryars et al. | 600/500 |
| 5,853,005 A * | 12/1998 | Scanlon | 600/459 |
| 5,964,720 A * | 10/1999 | Pelz | 600/595 |
| 6,068,589 A * | 5/2000 | Neukermans | 600/529 |
| 6,195,008 B1 | 2/2001 | Bader | |
| 6,198,394 B1 | 3/2001 | Jacobsen et al. | 340/573.1 |
| 6,248,064 B1 | 6/2001 | Gopinathan et al. | |
| 6,261,237 B1 | 7/2001 | Swanson et al. | 600/527 |
| 6,312,387 B1 | 11/2001 | Nissila et al. | |
| 6,315,719 B1 | 11/2001 | Rode et al. | |
| 6,375,621 B1 | 4/2002 | Sullivan | |
| 6,402,691 B1 | 6/2002 | Peddicord et al. | |
| 6,413,223 B1 | 7/2002 | Yang et al. | |
| 6,415,033 B1 | 7/2002 | Halleck et al. | |
| 6,425,872 B1 | 7/2002 | Hagiwara et al. | |
| 6,440,082 B1 | 8/2002 | Joo et al. | |
| 6,475,153 B1 | 11/2002 | Khair et al. | |
| 6,485,441 B2 | 11/2002 | Woodward | |
| 6,491,647 B1 | 12/2002 | Bridger et al. | |
| 6,494,829 B1 | 12/2002 | New, Jr. et al. | |
| 6,497,658 B2 | 12/2002 | Roizen et al. | |
| 6,506,153 B1 | 1/2003 | Littek et al. | |
| 6,540,673 B2 | 4/2003 | Gopinathan et al. | |
| 6,547,743 B2 | 4/2003 | Brydon | |
| 6,554,773 B1 | 4/2003 | Nissila et al. | |
| 6,565,515 B2 | 5/2003 | Ogura | |
| 6,575,902 B1 | 6/2003 | Burton | |
| 6,575,915 B2 | 6/2003 | Nissila et al. | |
| 6,575,916 B2 | 6/2003 | Halleck et al. | |
| 6,579,232 B2 | 6/2003 | Sakamaki et al. | |
| 6,599,251 B2 | 7/2003 | Chen et al. | |
| 6,600,949 B1 | 7/2003 | Turcott | |
| 6,689,069 B2 | 2/2004 | Bratteli et al. | |

FOREIGN PATENT DOCUMENTS

| | | | |
|---|---|---|---|
| GB | 2166871 A | * | 5/1986 |
| GB | 2252827 | | 8/1992 |

OTHER PUBLICATIONS

Scanlon, Michael, "Acoustic Sensor For Health Status Monitoring", 1998, *IRIS Acoustic and Seismic Sensing,* vol. II, pp. 205-222.

Bass et al., "Getting Two Birds with One Phone: An acoustic sensor for both speech recognition and medical monitoring", 138th Meeting of the Acoustical Society of America, Columbus, Ohio, Nov. 2, 1999.

Contract Agreement between The Henry M. Jackson Foundation for the Advancement of Military Medicine and Oceanit Laboratories, Inc. (Effective Date: Jan. 10, 1997) 36 pages total.

J. Siivola, *New Noninvasive Piezoelectric Transducer for Recording of Respiration, Heart Rate and Body Movements,* Medical & Biological Engineering & Computing, vol. 27, No. 4, Jul. 1989, pp. 423-424.

* cited by examiner

PASSIVE PHYSIOLOGICAL MONITORING (P2M) SYSTEM

This application claims benefit of provisional appllication 60/153,679 filed Sep. 14, 1999.

BACKGROUND OF THE INVENTION

Minimization of the time between injury occurrence and transport to the appropriate level of medical care is necessary to ensure that wounded and sick soldiers obtain the prompt medical attention essential for their survival. During that time, aeromedical care in a MEDEVAC™ medical evacuation helicopter environment is used to identify and transport casualties.

Military units conduct aeromedical evacuations daily during times of war and peace, exposing the patient and flight/medical crew to noise or environmental stress and difficult monitoring conditions. As in the civilian community, military nurses depend on reliable and efficient monitoring devices to provide accurate patient care in various environments, some of which are hostile and obtrusive to the use of conventional monitoring instrumentation. While aeromedical evacuation is a life-saving process for many, it is nearly impossible for medical personnel to monitor vital signs in a high noise environment.

Vital signs monitoring is normally a simple and routine procedure involving collection of pulse, respiration and blood pressure data. In a relatively quiet environment, these parameters are easily detected. However, acquisition of physiological signals of interest in a helicopter environment is a challenging problem for several reasons. Limitations on vital signs collection include high noise, vibration, auditory distractions, ineffective monitoring equipment, cramped working conditions, bulky gear during air evacuation, and electromagnetic interference with aircraft systems caused by some medical equipment. The additional complexity of leads and electrodes compounds the noise and environmental problems. The physiological parameters of vital signs fall within the helicopter-generated frequencies. Helicopter frequencies have a much greater power in those frequencies as well. Vibrational and acoustic artifacts are also major problems. The signal to noise problem must therefore be solved by other means in addition to low and high band pass filtering approaches. Due to the limiting work conditions, medical personnel cannot use a stethoscope to accurately monitor heart activity or blood pressure.

The military medical system needs a portable, non-invasive device capable of monitoring a soldier's vital signs in the field environment under less than ideal circumstances. This system needs to be useful to military medical personnel across the spectrum of care delivery, such as in mass casualty situations, aeromedical evacuations, ground ambulance transports, hospital wards, and intensive care units. A recent study found that thirty-two percent of aircraft medical devices flown onboard a rotor-wing MEDEVAC aircraft failed at least one environmental test.

Quartz crystals are minerals that create an electric field known as piezoelectricity when pressure is applied. Materials scientists have found other materials with piezoelectric properties. The versatility and potential uses for piezoelectric materials have been known but cost-prohibitive for some time.

However, recent decreases in the cost of manufacturing now permit greater application by engineers and researchers. The advantageous qualities of piezoelectric materials have been applied to medicine, security, acoustics, defense, geology and other fields. Development of applications with piezoelectric materials is in its infancy.

The medical practice and research application of piezoelectric-based instrumentation is gaining momentum. Piezoelectric methods have been successfully used in plethysmography, blood pressure monitoring by piezoelectric contact microphone, heart rate monitoring in avian embryos and hatchlings and piezoelectric probes. Piezoelectric materials are used as detectors of sensitive motion to measure human tremor, small body movements of animals in response to pharmacological manipulation, and respiratory motion for nuclear magnetic resonance (NMR) animal experiments. In combination with ultrasound, piezoelectric methods have been used to assess coronary hemodynamics, elastic tensor, intra-arterial imaging, and receptor field dimensions. In addition, piezoelectric transducers have been attached to the chest wall and used with automated auscultation devices and microcomputers for lung sound analysis. Piezoelectric film has been applied and studied to determine joint contact stress, and piezoelectric disks have been used for recording muscle sounds and qualitative monitoring of the neuromuscular block.

Stochastic wave theory, as commonly used in ocean engineering to analyze pseudo-periodic phenomena, indicates spectral peaks from respiration and heart rate. Human heartbeats, respiration, and blood pressure are repetitive in nature, reflecting complex mechano-acoustical events. However, various problems with piezoelectric instrumentation development prevent its full realization. Measurement of human tremor only works well when the environment is absolutely silent. In fact, extraneous noise such as equipment, fans, people talking, and the patient's own voice routinely exists in most hospital rooms. That noise masks and distorts the signal of interest, thus limiting the practicality of piezoelectric instrumentation. Animal noises make data collection difficult in laboratory animal studies. In non-laboratory environments, medical uses of piezoelectric instrumentation for humans remains a problem because of the inherent signal-noise problem.

A primary mission of military nurses is to ensure that wounded and sick soldiers obtain prompt medical attention and/or evacuation to definitive medical care. The actions performed during the time period between a battlefield injury and the transfer of casualties to appropriate medical treatment is critical for the welfare of the soldier, and can be the difference between life and death. It is during this critical time period where diagnosis and treatment begins and also when evacuation—for example via MEDEVAC™ medical evacuation helicopter—occurs.

Unfortunately, the extremely high noise and vibration inherent in the helicopter environment prevents nursing and medical personnel from accurately measuring vital signs. Not only are electronic medical monitors rendered ineffective with the high vibrations; traditional methods of measuring pulse and blood pressure using a stethoscope become unreliable in the high noise. Cramped working conditions and bulky gear during air evacuation exacerbate these problems.

Most conventional methods use devices that employ electrodes, leads, wires, and cuffs to measure one or more vital signs, for example, blood pressure machine, ECG monitor, pulse oximeter. Existing monitors require some sort of attachment and thus are not passive. In addition, conventional equipment is highly sensitive to noise, such as a helicopter or airplane engines and rotors.

Clearly, what is needed for this common situation is a monitor that can consistently and accurately measure vital signs during a medical evacuation where there is high noise and vibration. The monitor being relatively autonomous intervention by a nurse or technician is not required. With the added capability of telemetry for remote monitoring and communication, information may be forwarded in real-time via wireless communication to the destination where medical personnel and other caregivers are located.

Needs exist to develop better methods and apparatus for physiological monitoring.

SUMMARY OF THE INVENTION

The present invention is known as Passive Physiological Monitoring, $P^2M$, or simply P2M. Data records with vast information, such as blood pressure, are measured, recorded, and may later be delineated to determine the physical condition of the subject being monitored.

Recent developments in materials science and data processing have created the potential for a new monitoring device using piezoelectric film, an electrically active fluoropolymer. Although the medical applications of piezoelectric film are still at the infant stage, the testing of medical instruments is promising.

The cardiovascular system is modeled as a system of pipes, pumps, and other appendices, with the engineering phenomenon known as "water hammer" as the basis for a working model for data analysis in the calculation of blood pressure.

"Water hammer" is a compression wave transmitted through the household plumbing network of pipes and valves when household water is abruptly shut off. The result is a noticeable sound and the deterioration of the plumbing system. Water hammer is caused by the increase in pipe pressure caused by sudden velocity change, typically after water is shut off during a valve closing. The compression wave is described as follows:

$$c = \frac{1}{\rho} * \frac{dP}{dV} \qquad (1)$$

where
c=speed of the compression wave (ft/sec);
dV=change in velocity ($V_{initial}-V_{final}$);
$\rho$=density of the fluid; and
dP=change in pressure.

Skalak (1966) applied the linearized theory of viscous flow to develop a basis for understanding the main waveform features in arteries and veins. The vascular system is equivalent to a network of non-uniform transmission lines.

Womersly (1957) had applied those principles to a single uniform tube representing an arterial segment and compared the results to the experimental data taken in a dog, prior to Skalak's theory. Good agreement was reported between the measured flow and the flow computed from the measured pressure gradient.

Anliker (1968) showed that the dispersion phenomena associated with waves propagating in blood vessels are potential measures of the distubility of the vessels and other cardiac parameters. Anliker assumed that vessels behave like thin-walled cylindrical shells filled with inviscid compressible fluid. More complete models have provided good agreement.

Karr (1982) studied pressure wave velocity on human subjects and developed a method to determine the pulse propagation speed. The invention recognizes that such information may be used to determine plaque buildup, cholesterol concentration on the arterial wall, and arterial wall thickness.

Equation (1) allows for determination of pressure change (dP) from the heart pulsing based on the dispersion relationship between pulse wave velocity (c) and flow velocity (v). Karr's method measures flow velocity to determine dP, which is related to systolic pressure (pS) and diastolic pressure (pD).

The new invention measures the pressure energy from heartbeat and respiration collectively. The heart contribution to the energy spectrum is determined by removing the respiration contribution to the energy spectrum. Respiration energy is filtered out by comparing the energy spectrum calculations of velocity with velocity measures using electromagnetic and doppler methods. Since the sympathetic tone may influence blood pressure measurement accuracy, the new monitor can be configured for one of its piezoelectric sensors to serve as a dedicated doppler sensor that uses ultrasonics to adjust interpretations of data as a function of the sympathetic tone of the patient. The selective omission of P2M signals and the selective comparison of P2M sensor data with data from other parts of the body, as well as comparisons between two or more simultaneously triggered sensors, isolates energy contributions from the heart. P2M energy spectra determined from the foot differs from spectra derived from the chest area, which provides a means for isolating heart energy as the foot spectra is largely void of energy from respiration.

Once velocity (v) is known, the relation between systolic and diastolic blood pressure (2) and the Bernoulli equation (3) is used to measure blood pressure. The Bernoulli equation is a fundamental relationship in fluid mechanics that is derived from Newtonian mechanics and the principle of conservation of energy. A more compressive version of the same equation can be developed to reflect more complicated non-steady flows.

$$p = pD + \frac{1}{3} * (pS + pD) \qquad (2)$$

where
pS=systolic pressure;
pD=diastolic pressure; and
p=average pressure.

$$p = \rho g h + \frac{1}{2} * \rho * V^2 \qquad (3)$$

where
$\rho$=fluid density,
g=gravitational constant, and
h=height, head energy term.

From these equations we can develop expressions for pD and pS, both as a function of the pulse wave velocity (c), flow velocity (v) and pulse wave pressure (dP):

$$pD = \frac{1}{2} * \rho * v^2 - \rho * C * dV \qquad (4)$$

$$pS = pD + \rho * C * dV \qquad (5)$$

P2M is well-suited to assist medical personnel in several areas including, but not limited to, the following situations:
  (1) Medical monitoring of vital signs of severely injured persons in high noise and vibration environments such as rescue helicopter where current monitoring techniques are cumbersome or impossible;
  (2) Monitoring casualties resulting from major disasters such as aircraft accidents, earthquakes and floods;

(3) Physiological monitoring of large numbers of patients through a "smart stretcher" easily deployed for field use by medical personnel;

(4) Continuous military hospital bed monitoring without disturbing patients; and (5) Patient monitoring when treatment is delayed due to temporary overload of medical facilities.

The development of the P2M or a passive sensor array (multi-sensor system) is a significant innovation in passive monitoring. Through the use of a grid of passive sensors, noise can be reduced through correlating signals from different pads to discern noise from biological signals. This is very important in high-noise environments. Additionally, the significance of a passive multi-sensor system is that it affords the opportunity to more comprehensively monitor a patient. As a tool, the grid of passive sensors provides an innovative way to monitor patients in adverse ambient conditions. The system provides a tool whereby parameters other than blood pressure, heart rate, and respiration can be measured. These parameters include, but are not limited to, patient movement and sleep habits, pulse strength over various portions of the body, relative blood flow volumes, and cardiac output, among others.

The main components of the Passive Physiological ($P^2M$) system are the passive sensor, hardware for amplification, filtering, data-acquisition, and signal-analysis software. In a preferred embodiment, the single passive sensor has dimensions 8"×10" and is preferably encased in a protective covering. Leads from the sensor attach to the electronics (amplifier, filter, data-acquisition card, desktop computer) where the raw analog voltage signal is filtered and amplified and converted to digital form. Digital filtering and software manipulation of the data in the form of frequency analyses are then performed. Finally, signal processing techniques are then used to extract physiological information from the digital signal.

The sensor pad is preferable placed directly beneath the back of a patient lying supine on a MEDEVAC™ medical evacuation litter. The mechanical/acoustic signals created by cardio-pulmonary function are transmitted through the body onto the passive sensor, which converts the signal into an analog voltage. An illustration of the existing P2M setup is shown in FIG. 6. Among the major hardware used for the laboratory setup are: desktop computer, a multi-function programmable charge amplifier and roll-around rack to encase all of the hardware. To maintain versatility for initial research and development, most of the equipment were chosen for functionality at the expense of space efficiency.

It is an object of the present invention to provide the military medical community with an inexpensive, non-restrictive, portable, light-weight, accurate, and reliable device that can be used in field or fixed facilities to provide an accurate measurement of heart rate, respiration and blood pressure in high noise and vibration environments and thus improve medical care in mass casualty situations, aeromedical evacuations and hospital settings.

It is an object of the present invention to adjust the signal noise to enable the use of piezoelectric instruments in aeromedical transport of patients, hospital bed monitoring, and other applications in the military and civilian medical environment.

It is an object of the present invention to develop a prototype physiological monitor using piezoelectric film in various field environments. The variables of accuracy, precision, user characteristics, and patient comfort determine the value of a field instrument for collection data on vital signs.

It is an object of the present invention to provide a non-invasive means for monitoring vital functions without the use of electrical leads or wiring on the patient. The use of the human body's acoustic and electromagnetic signals to determine heart rate, respirations, and blood pressure.

These and further and other objects and features of the invention are apparent in the disclosure, which includes the above and ongoing written specification, with the claims and the drawings.

DETAILED DESCRIPTION OF PREFERRED EMBODIMENTS

The preferred P2M system is a monitoring device with two major subsystems, one to measure signals and the other to process data into meaningful information.

Figure 1:
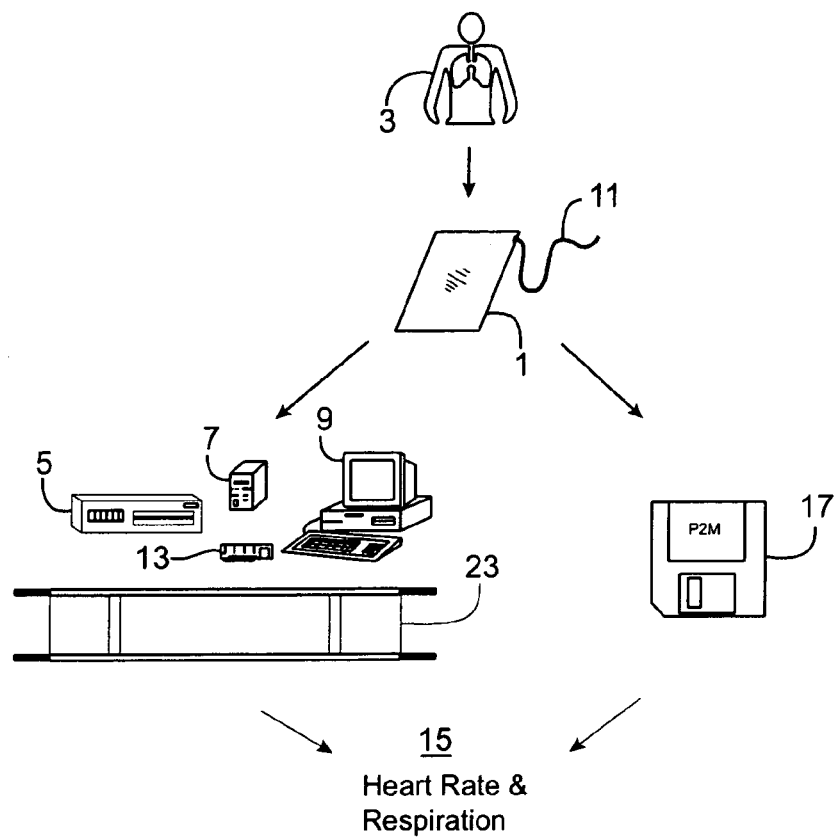
FIG. 1 is a schematic of the P2M system components.
Figure 2:
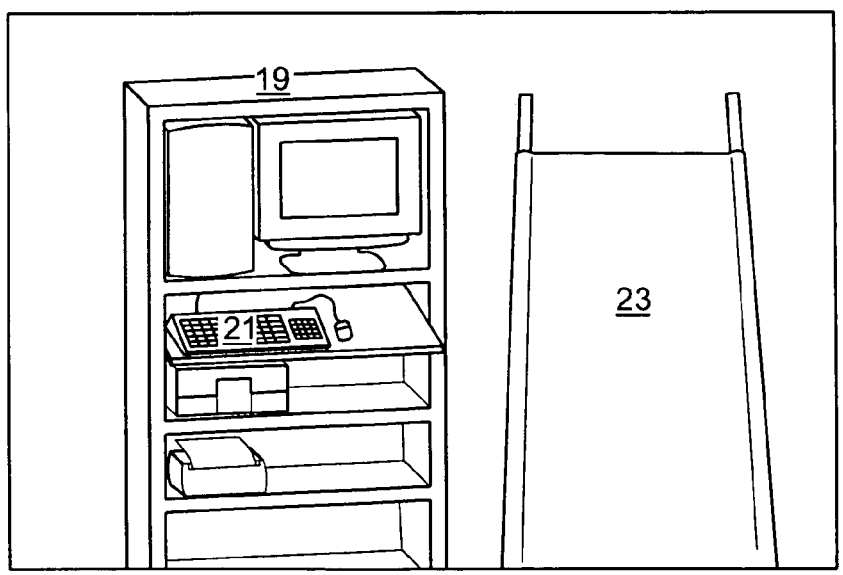
FIG. 2 is a perspective view of the P2M system.

FIG. 1 shows a schematic of the system, and FIG. 2 shows a perspective view of the system. First, the piezoelectric film, an electrically active fluoropolymer converts mechanical energy such as movement caused by a heartbeat into voltage measurements capable of supporting time series analysis techniques. Second, the voltage is recorded by and analyzed using a microcomputer controlled system, the purpose of which is to discriminate the signal from background noise and display it on a screen or printout. Techniques such as preamplifying and preconditioning through the use of high and low-band pass filters reduces noise.

The piezoelectric material 1 used is the polymer polyvinylidene fluoride (PVDF), which can be shaped into cables, thin film, or thick tiles. PVDF piezoelectric film is environmentally rugged, lightweight, flexible, inherently reliable, sturdy, easily repairable and transportable with excessive assembly or disassembly. Since the material is inert, it may be used inside the human body. Ultraviolet radiation passes harmlessly through the PVDF film, which may be produced in varying thicknesses. In addition, the piezoelectric film is waterproof, operates between 0 and 145 degrees Centigrade, and does not tear under stress. PVDF may convert a temperature reading into an electric output. The PVDF film is incorporated into a fluid-filled vinyl pad, approximately 10 cm by 10 cm in surface area. This is placed on/under/above various locations of the patient.

P2M detects cardiac and respiratory motion, and monitors pulse, respiration and apnea episodes 3. Cardiac and respiratory movements are simultaneously recorded by selective filtering of original signal. The piezoelectric element 1 is a pressure-sensing detector acting as a highly sensitive strain gage providing high dynamic range and linearity. Analog signals are fed through a band-pass filter into an amplifier (x 200–x5000) 5 and are visually displayed. Analog acoustic signals are converted to digital values using a multi-channel converter 7 at a sampling rate of up to 5 kHz. Data is transformed to the frequency domain using Fast Fourier Transform (FFT). The system uses a microcomputer 9 for recording, analysis and presentation of data, which allows for on-line assessment of data and realtime decisions.

In its simplest mode of operation PVDF piezoelectric film 1 acts as a piezoelectric strain gage. The voltage output is up to four orders of magnitude higher than that produced by a nonamplified signal from circuitry used with resistive wire. Linearity and frequency response are excellent. Although similarities to a strain gage exist, current need not be applied since the device is electrically self-generating. Unlike the strain gage, the present invention does not produce an electric charge ad infinitum with sustained stress. The slowest frequency the polymer film detects is a thousand seconds for an electrical event to occur, and the highest is one gigahertz (microwave). The piezoelectric film is passive and biologically non-hazardous, as opposed to traditional strain gages that require an applied current.

PVDF sheets are commercial off-the-shelf (COTS) products, the type and specifications of which were chosen based on optimum sensitivity range and resilience. Each sheet contains seven-foot attached shielded twisted-pair (for noise rejection) leads 11 to transmit the charge produced by the sheets.

The piezoelectric sheets 1 are placed under a patient's chest and foot or at similarly remote areas of the body, or may be put on like a wrapped cuff. The change in pressure exerted by the patient's respiration and heartbeat causes the piezoelectric film to generate voltages, which is carried via nonmagnetic miniature coaxial cable 11 through a radio frequency filter 13. The signal is then directed to a high input-impedance amplifier 5 and computer system 7 for data processing. A conventional oscilloscope and a chart recorder displays the output. Respiration and heart rate 15 are then calculated by the energy spectrum from the time series data.

Several techniques reduce noise and vibration interferences. Active cancellation uses two piezoelectric sensors, one of which is not in contact with the body. The sensor not attached to the body is exposed to environmentally acoustic and vibrational signals, while the sensor attached to the body is exposed to environmental as well as body signals. Subtraction of one output from the other output yields the body signal of interest.

Another preferred technique to reduce noise involves band-pass filtering/band-stop filtering. By identifying the extraneous electronic or acoustic noise and its particular frequencies, band-pass or band-stop filtering eliminates extraneous signals from the overall signal.

Additionally, signal processing techniques that use a prior knowledge of the expected signals extract the desired information from the piezoelectric signal. Spectral techniques help to identify the frequencies and amplitudes of the events of interest and discern them from extraneous noise.

Cardiac action analysis uses a bandpass frequency limit of 0.1–4.0 Hz, and respiration analysis uses a frequency limit from 0.01–3.0 Hz. The filtered cardiac and respiration signals are fed to a recording system. Body movements are analyzed by bandpass filtering the original signal with frequency limits from 0.1–20 Hz.

Once the signal produced by the film sensor is converted to voltages, amplified and filtered, it is processed through the P2M instrumentation. The hardware equipment includes, but is not limited to, a 586 processor computer 9 with enhanced RAM and disk capacity to handle large amounts of data. A board with a range that includes acoustic frequencies facilitates data acquisition, signal conditioning and signal processing.

For system operation, a master program 17 combines the three separate software modules of data acquisition/control, signal processing/analysis, and data display/user interface. The LABVIEW™ laboratory view "G" graphical programming language was used for all three subroutine programs. The analog voltage signal is digitized and analyzed in time and frequency domains. Routines developed for signal conditioning and analysis include digital filtering, spectral analysis, auto correlation, and noise-rejection programs. The data is displayed real-time in either Monitor or Acquisition mode. Monitor mode displays the current data and discards old readings as new updates are processed, while Acquisition mode saves data for future analysis. The voluminous data must not exceed the disk-storage capacity of the computer in Acquisition mode.

For protection and east of transport, the entire P2M system 19 is encased in a metal technical enclosure 21 with casters (not shown) and locking glass door (not shown), as shown in FIG. 2. The equipment also includes a MEDE-VAC™ medical evacuation stretcher 23 on which the sensor is mounted. This device may be incorporated into a litter to eliminate the need for patient attachment or miniaturized as a portable field device in a purse with a wireless communication setup.

Significant field and analysis testing was conducted to confirm the workability and accuracy of the P2M system. The piezoelectric film measures mechanical, thermal and acoustic signals. That high sensitivity is necessary to measure vital signals non-intrusively. For pulse rate, the physical beating of the heart is transmitted through the body into the piezo-film sensor pad as mechanical impulses. The respiration is measured by the mechanical impulse transmitted to the sensor based on chest movements. The sensitive piezo-film sensor pad measures all extraneous movement and speech, resulting in a voltage signal output that is superimposed upon the physiological signals. As a result, movement or speech by the subject may cause a reading error.

The P2M sensor measures all physical impulses in the measuring environment, including the patient's physiological signals, nearby human noise and activity signals, noise and vibration from the machinery, and electromagnetic (EM) noise emitted from the lights and instrumentation. While the output signal includes all of these signals, many are too weak to affect the measurement while others such as EM noise corrupt the reading. Running the signal through filters and other signal-processing algorithms removes the noise. The conditioned signal is then analyzed through routines, including a fast Fourier transform (FFT) which identifies the primary signal frequencies. For a still, speechless patient, the primary frequency is usually respiration, and the second highest frequency is heart rate. Patient positioning and frequency harmonics may complicate the distinction, requiring additional logic to separate and identify the heart and respiration frequency peaks. The logic algorithms must be robust enough to define the respiration and heart peaks for a variety of conditions.

To increase resolution, a large number of high sampling rate data points were selected and re-sampled at a lower rate to simplify computation for accurate analysis. The minimum sampling interval was thirty seconds.

Figure 3:
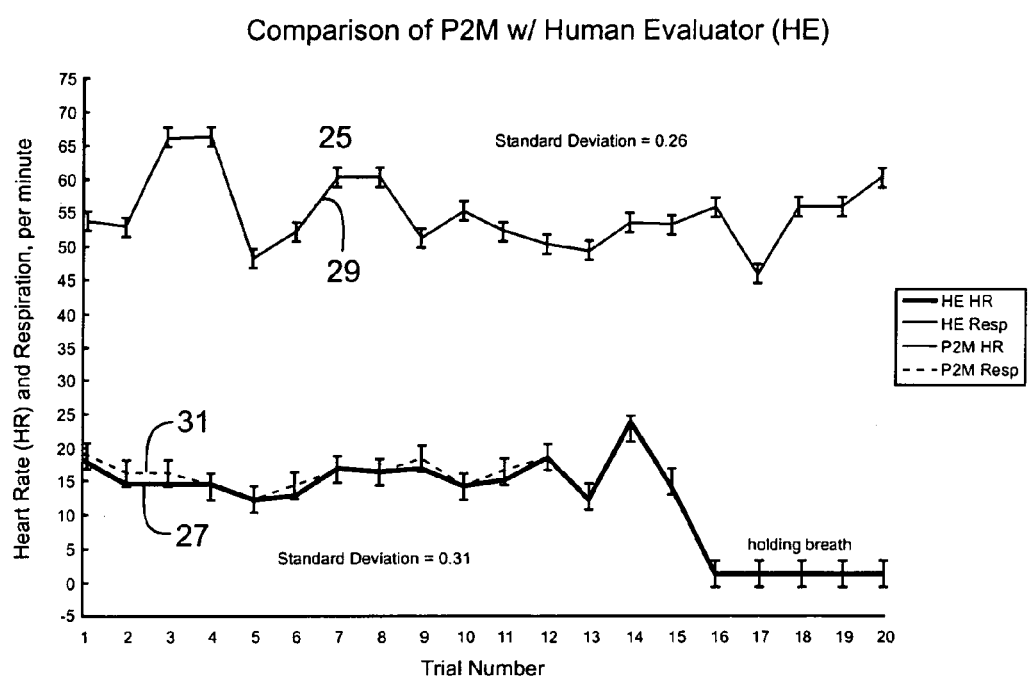
FIG. 3 is a graphical comparison of the P2M bench test results and the human evaluator measurements.

FIG. 3 shows the results for the twenty respiration/pulse-rate measurements performed with the P2M system. Human evaluator measurements were performed simultaneously as a control. P2M accurately measured pulse 25 and respiration 27 under ideal conditions, but patient movement or speech interfered with accurate measurement. Heart rate measurement quality was not reduced by the absence of respiration, and P2M matched the control measurement results 29, 31 with an error of less than beat per minute.

Figure 4:
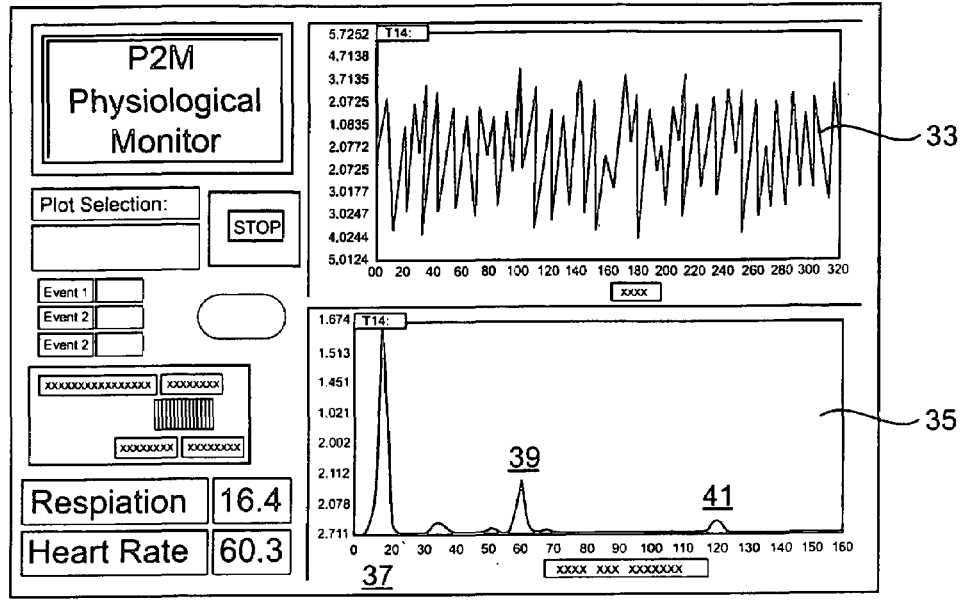
FIG. 4 is a front view of the front panel display and user interface of the P2M system in Acquire Mode.

FIG. 4 shows the P2M front panel in Acquisition mode. The upper graph 33 displays a thirty-second window of time-series measurements of all physiological signals. Heartbeat spikes are shown in the upper (time series) graph 33, along with a lower-frequency sinusoidal function which corresponds to the respiration signal. The lower graph 35 shows the same data in the frequency domain. The first and largest spike 37 corresponds to approximately 16.4 respirations per minute. The control group 31 measured 17±2 respirations per minute. The large amplitude of the spike indicates that respiration is the largest impulse measured by the sensor pad. The second-largest spike 39 is sixty times per minute, which was identical to the actual heart rate measured by a fingertip-clip heart-rate monitor. The power as measured by the amplitude is less than one-third of that found in the respiration frequency, but the ratio varies based on the physiology and sensor pad positioning of the patient. The smaller spikes 41 in the lower graph represent respiration and heart-rate harmonics, a result of the harmonics not being a perfect sinusoidal function. Since the heart rate might fall at exactly the same frequency as a respiration harmonic, it is necessary for logic algorithms to check for harmonics. The heart rate and respiration harmonics may be differentiated by comparing signals taken from different parts of the body.

The buttons and menus 43 on the front panel of the interface program enables the control of data acquisition and analysis routines. The thirty-second data records may be saved to file for archiving or additional evaluation.

Figure 5:
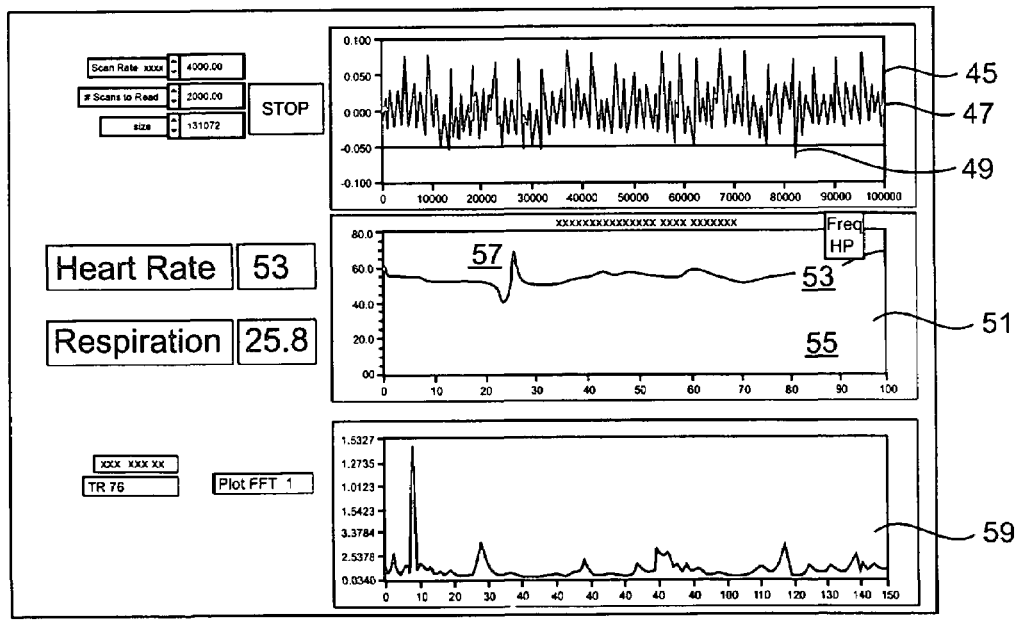
FIG. 5 is a front view of the front panel display of the P2M system in Monitor Mode.

FIG. 5 shows the P2M system in Monitor mode. The top graph 45 shows the time-series data, with the characteristic higher-frequency heartbeat spikes 47 superimposed over a lower-frequency respiration wave 49. The middle graph 51 shows heart rate 53 and respiration 55 as updated every five seconds. As a new five-second data string is acquired, the oldest five seconds of data is discarded, and the heart rate and respiration are re-calculated by analyzing the thirty-second data string with the new data. The upper curve 53 is colored red to signify heart rate, while the lower curve 55 is colored blue to signify respiration. Heart rate appears steady in the mid-50s range, with respiration in the mid-teens. Both compare favorably (±2) with human control measurements. The anomaly 57 after 25 updates is attributable to patient movement or an extraneous and errant noise/vibration event. The bottom graph 59 shows an FFT of the time-series signal.

Regular voltage signals of heart beat provide strength signals as voltage levels that are related to blood pressure. Times between signals at varied parts of the body or patterns of secondary signals provide information on circulation or blockage or interference with blood flow.

Figure 6:
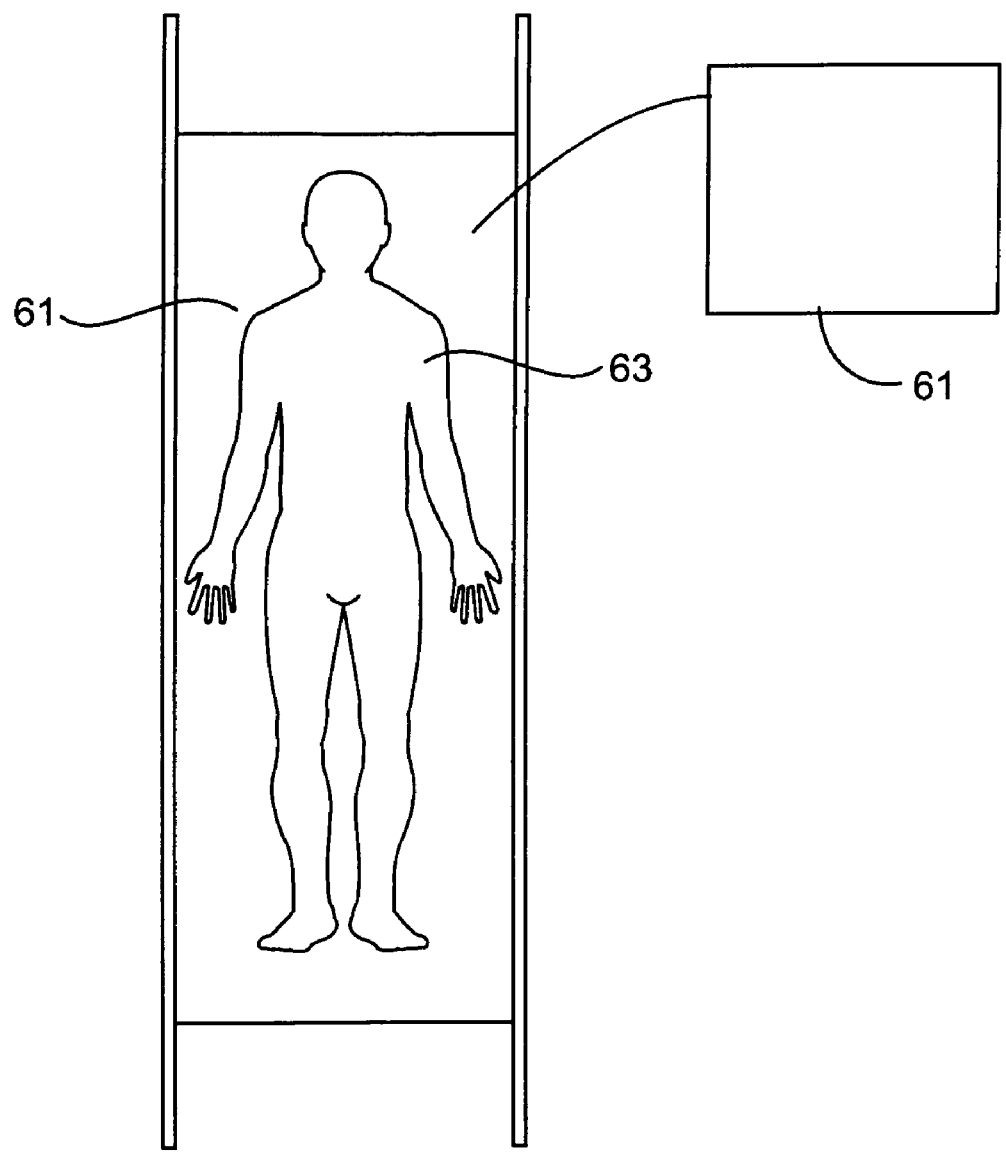
FIG. 6 is a schematic view of a preferred embodiment of the P2M sensor.
Figure 7:
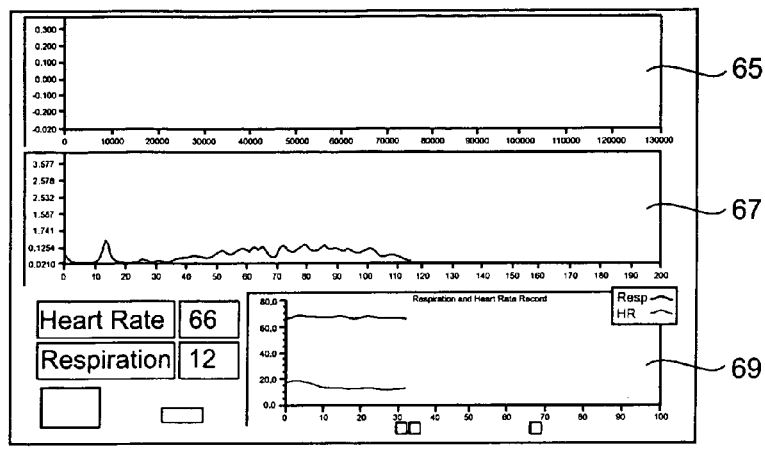
FIG. 7 shows one of the graphical user interfaces (GUI) of the P2M system.

In another preferred embodiment, FIG. 6 shows a schematic view of the P2M system with a single passive sensor 61 positioned on a patient 63. FIG. 7 shows one of the graphical user interfaces (GUI) of the P2M system. The upper chart 65 shows a 30-second window of digital voltage data, where the low-frequency oscillations are caused by respiration and the higher-frequency spikes are the result of heartbeat measurements of the patient on the litter. The time-series signal is converted to frequency data via a Fourier transform and displayed as a power spectrum, shown in the middle chart 67. From this data, pulse and respiration can be extracted by examining the power associated with the dominant frequencies 69.

In a preferred method of blood pressure measurement passive measurement of blood pressure (systolic and diastolic) may be conducted using pulse wave analyses. Measurement and characterization of the pulse-wave velocity (PWV), or alternately, the pulse-wave travel time (PWTT), inherently requires more than one measurement location. Thus, plural sensors are required for measurements in different locations. The sensors may measure pulse-wave characteristics, for example, along the brachial artery, along with other measurements described herein.

Figure 8:
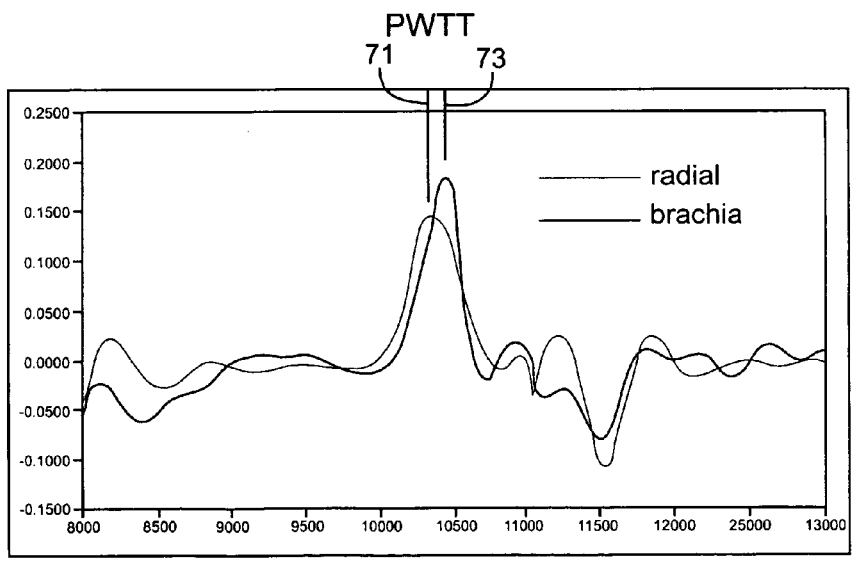
FIG. 8 shows the graphical user interface of the P2M system showing time-series and frequency-domain representations of physiological data.

FIG. 8 shows measurement results of the pulse at two locations along the arm. The temporal separation between the two corresponding peaks 71, 73 gives the Pulse-Wave Travel Time (PWTT). This value can be used to correlate systolic and diastolic blood pressure. As such, the calibration must be performed simultaneously for several measurements of PWTT and blood pressure to construct a calibration curve. Barschdorff & Erig showed that the relationship between blood pressures (systolic and diastolic) are approximately linear with PWV and PWTT.

Figure 9:
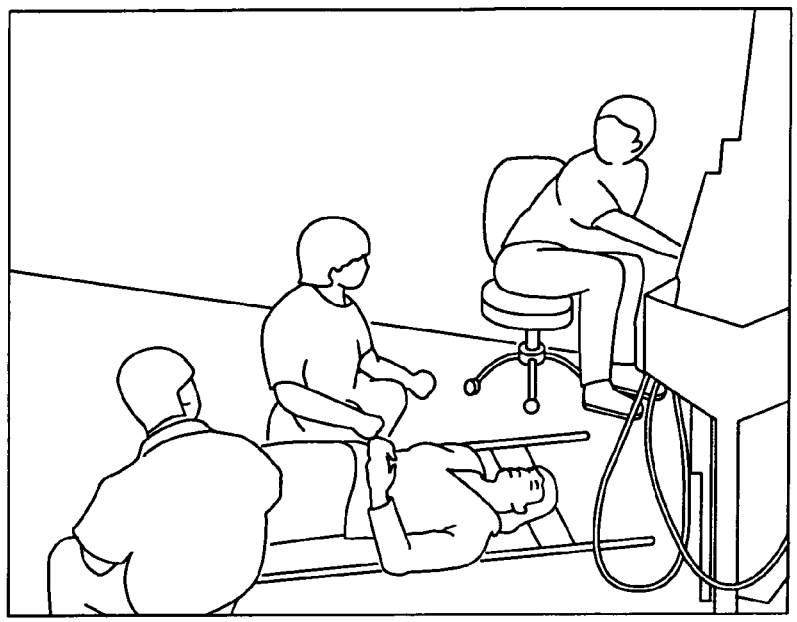
FIG. 9 shows measurement of Pulse-Wave Travel Time (PWTT).

Testing and evaluation of the P2M system was performed at TAMC in February, 1998. Simultaneous measurements of pulse and respiration were performed with the P2M, an electronic monitor, and by human evaluation. FIG. 9 shows a photograph of the testing performed at TAMC. A total of 11 volunteers were monitored following the project's testing protocol.

Figure 10:
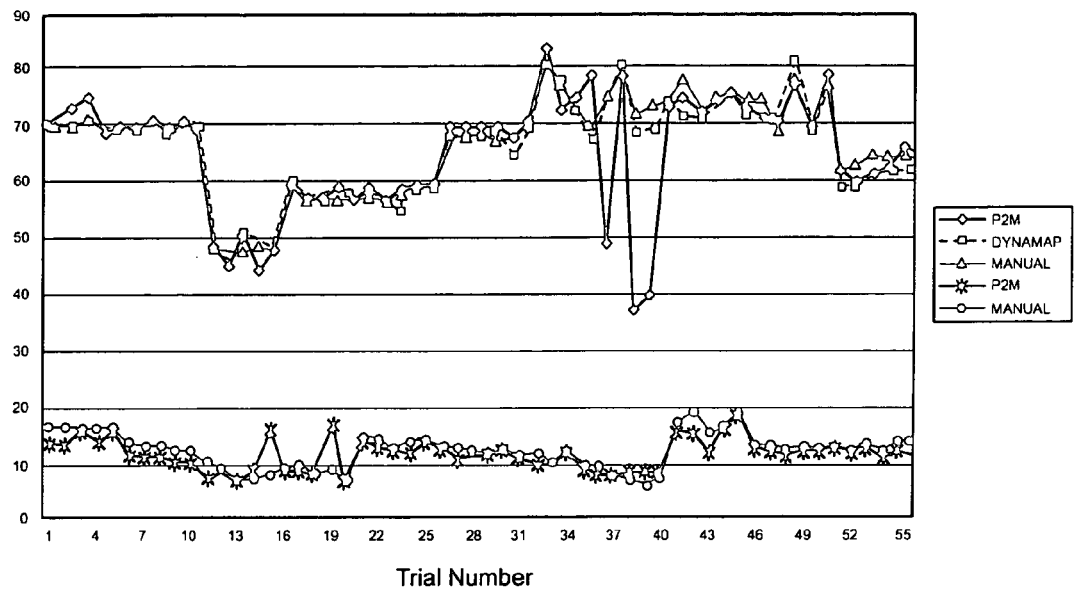
FIG. 10 shows a system test and evaluation results in a graph.

FIG. 10 displays the results of the testing. The P2M was over 95% accurate as compared to conventional methods, and the several instances where the P2M was not in agreement with conventional methods proved to be very valuable in subsequent modifications and improvements to the system software. In addition, 12 volunteer nurses performed physiological monitoring of pulse and respiration using the P2M, electronic monitor, and human evaluation. Following the monitoring, the nurses completed a survey comparing and ranking the usage of the three methods.

Testing of the P2M system for pulse and respiration in a high noise and vibration environment was performed at Wheeler Army Air Field, on Mar. 5, 1999. Tests were performed during static display of a MEDEVAC™ medical evacuation helicopter. The main purpose of the test was to characterize the high noise/vibration environment using P2M, microphones and accelerometers. Results showed that through filtering and signal analyses, the P2M was able to discern physiological signals from the high amplitude and frequency noise caused by the helicopter to output accurately pulse and respiration. No conventional methods were performed at this test due to the high-noise environment, which would render those methods useless.

Figure 11:
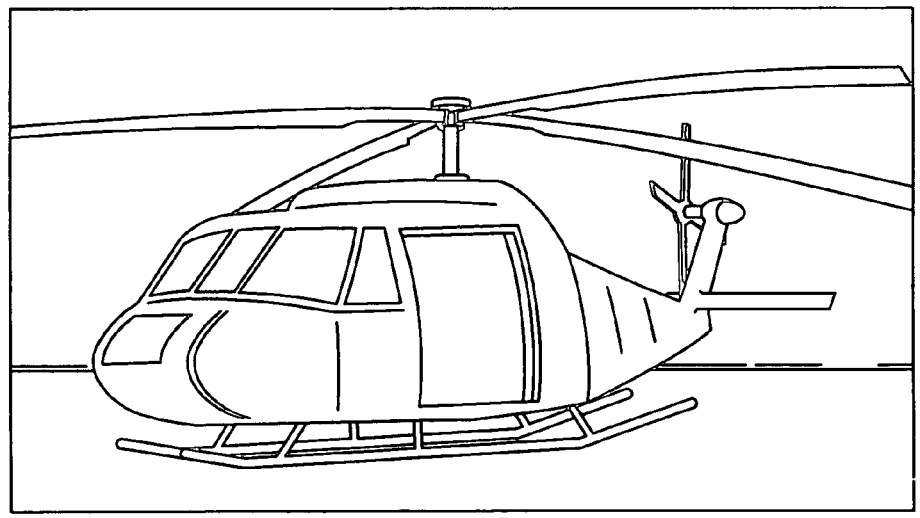
FIG. 11 high noise and vibration testing of the P2M at Wheeler Army Air Field.
Figure 12:
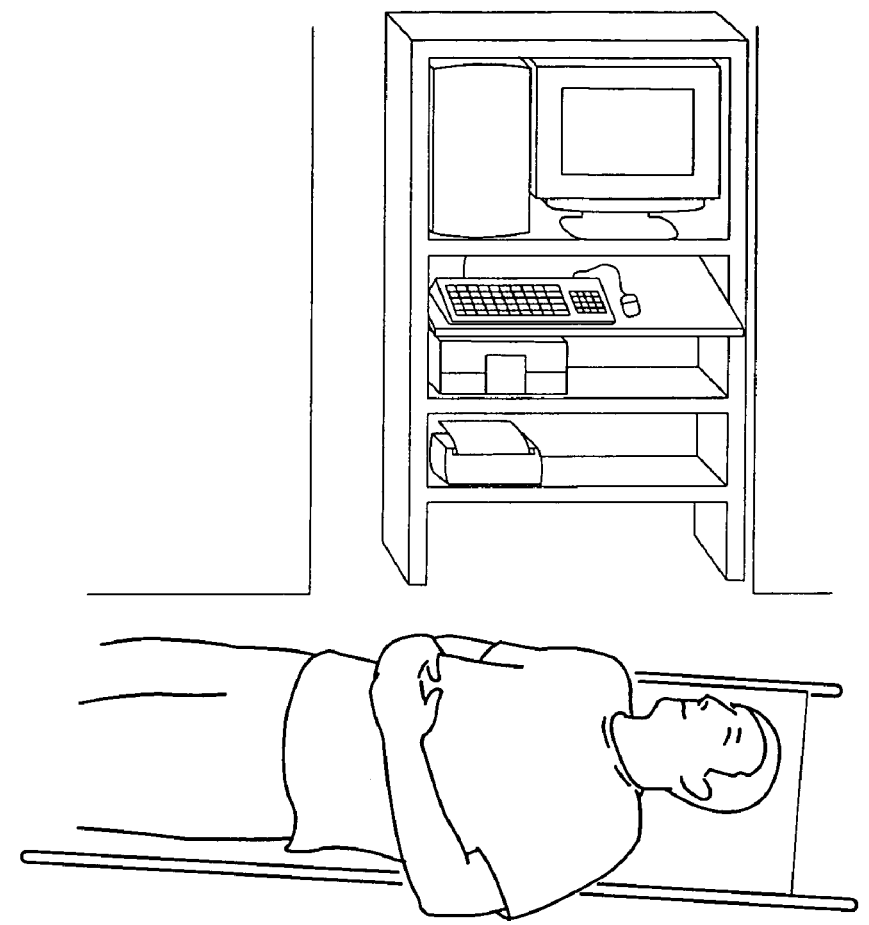
FIG. 12 shows the measurement through a body armor.
Figure 13:
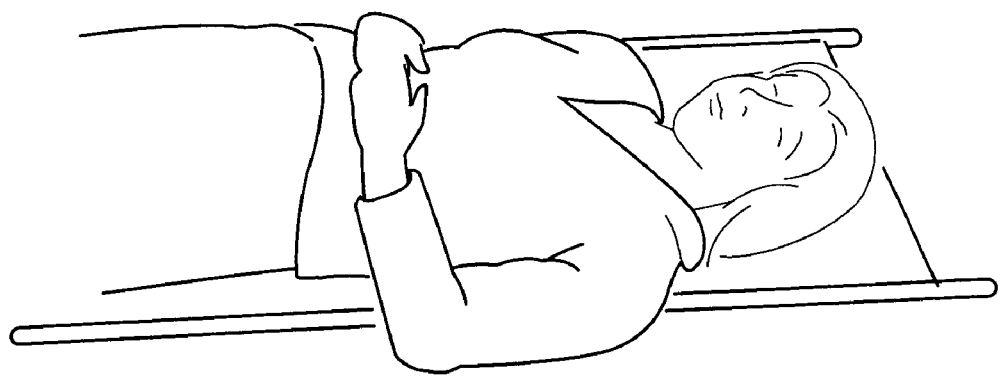
FIG. 13 shows testing through body armor and MOPP gear combined.

FIG. 11 shows the high noise and vibration testing of P2M at Wheeler Army Air Field, on Mar. 5, 1999.

Next, in response to inquiries made by the flight medics during the Mar. 5, 1999 testing at Wheeler, the ability of P2M system to accurately monitor pulse and respiration through layers of clothing and gear was tested. Fragmentation protective body armor, Military Oriented Protective Posture (MOPP) gear, and a combination of the two were tested using the P2M system. Results showed that the P2M performed with higher fidelity with the additional layers between the subject and the sensor, which is largely due to the increased contact area and efficient transmission of mechanical and acoustic signals through the solid layers.

The single-sensor $P^2M$ configuration that has been demonstrated to accurately measure pulse and respiration is very sensitive to the patient position relative to the main sensor pad. The quality and magnitude of the physiological signals received by the system depends on this positioning. The preferred optimum placement is to situate the sensor directly beneath the center of the patient's chest. If the sensor is moved from this placement, or if the patient position changes, the integrity of the incoming signal also changes. Thus, a preferred configuration uses multiple sensors in a pattern that covers the entire region of the litter on which the patient would lie so that regardless of patient movement and position, there will always be one or more active sensors in optimum measurement placements.

In a preferred embodiment, the invention is a passive system using an array of distributed sensors (or "multi-sensor") capable of accurately and robustly monitoring certain physiological signals of the human body. These signals, in turn, may be processed for determination of vital signs that are currently used by nurses and other caregivers, for example, heart rate, respiration, and systolic/diastolic blood pressure.

Passive monitoring of such parameters as cardiac output, cardiac function, and internal bleeding are within the scope of this invention. The invention uniquely provides a device that is passive (completely non-invasive), unobtrusive, and autonomous; i.e., the apparatus in no way interferes either with the patient's mobility or with other monitoring equipment, and is capable of functioning with a minimum of technical expertise. In addition, the equipment functions reliably in high-noise environments and other situations that render alternative and existing methods ineffective. These environments include, but are not limited to, medical evacuation (MEDEVAC™ medical evacuation) by helicopter or ambulance, and operation through Military Orientated Protective Posture (MOPP) gear and body armor.

With the development of a reliable multi-sensor monitoring system for such rugged and noisy operation, the application to the hospital ICU environment, where noise is substantially lower, is considerably more straightforward. Completely non-invasive, passive, pulse, respiration, blood pressure (and detection of cardiac output, internal bleeding, shock, etc.) measurements using a sensor system that is undetectable to the patient have considerable intrinsic value even in noise-free surroundings. The passive and autonomous operation of such a system is suitable for telemetry and real-time remote monitoring, and the final feature of the invention is a telemetry design feature for distance and remote monitoring.

Figure 14:
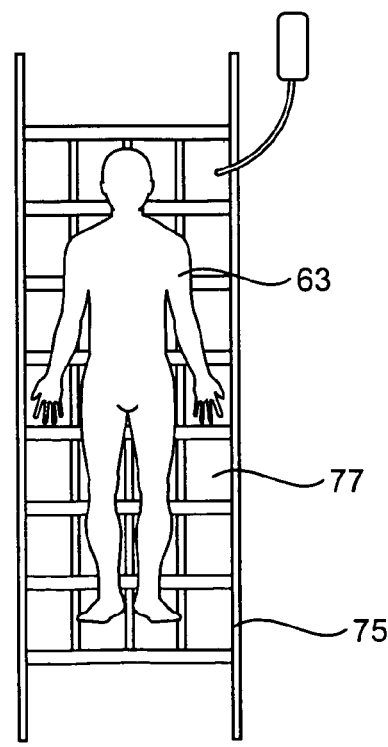
FIG. 14 shows schematic view of the Passive Physiological Monitoring (P2M) System Using a passive sensor array and microelectronics incorporated into a MEDEVAC™ medical evacuation litter.

FIG. 14 shows a schematic of the P2M using a passive sensor array and microelectronics incorporated into a MEDEVAC™, medical evacuation litter. A schematic of the inventive technology, incorporated into a MEDEVAC litter, is shown in FIG. 14 below. The litter 75 is covered in an array 77 of 32 sensors, each of which can measure acoustic and hydraulic inputs from the patient 63. Each of these signals contains a measure of physiologically generated signal and environmental noise. The environmental noise on each pad will be similar, whereas the physiologically generated signals may be position dependent. This information is used to separate the signal from the noise using proven techniques. Position dependent physiological signals are used to determine patient position, heart rate, respiration, blood pressure, pulse strength distribution, and potentially some measure of cardiac output.

The invention may be incorporated into a wide range of applications apart from the MEDEVAC™ medical evacuation litter. The passive sensor array may be configured without much change to operate on a hospital bed or an ordinary mattress used at home. Of particular note is the area of premature infant care. In this case, the attachment of sensor leads to the infant may often be difficult, causing irritation of sensitive skin and entanglement in leads. The sensor may be incorporated into equipment for use in both civilian and military sectors. The sensor may be incorporated into field equipment, clothes and uniforms. This includes, but is not limited to, cervical collars, body armor, biological and/or chemical hazard protection suits, extraction devices, clothes, cushions and seats and seatbacks. Exercise equipment, such as stationary bicycles, treadmills or steppers may benefit by incorporated sensors into the supports.

Physiological indicators such as heart rate may be detected through handholds as an aid to regulating the exercise regime. Other useful applications might include the use of a passive sensor system in a chair or couch used for psychological examinations. Scrutiny of the subject's physiological signs may give indications of emotional disturbance caused by trigger words or events during counseling. The size of each sensor, number of sensors in the array, and configuration of the sensor array may be tailored, without much experimentation, to particular needs and situations. For a mattress, for example, 32 or more sensors in a rectangular array may be required.

The preferred passive sensor may use piezo-electric films and ceramics, hydrophones, microphones or pressure transducers. Amplification hardware may include signal amplification circuitry and hardware, e.g., charge amplifier. Data acquisition hardware and signal processing hardware (circuitry) and software are used in the system. For the interface between sensor and patient either solid, fluidized (air) or fluid layer may be used, as for example, gel, water, foam, rubber, plastic, etc. The interface facilitates transmittal of physiological signals.

The invention has great medical value for field monitoring, hospital monitoring, transport monitoring, and home/remote monitoring. For example, the invention may have application in every hospital for passive monitoring of patients. The invention being undetectable to the patient, which adds comfort to the monitoring process.

While the invention has been described with reference to specific embodiments, modifications and variations of the invention may be constructed without departing from the scope of the invention.

We claim:

1. A method for passively monitoring physiology of a patient, the method comprising:
   engaging a first piezoelectric sensor with the patient by coupling the patient with a patient supporting surface including the first sensor;
   engaging a second piezoelectric sensor in a location for sensing environmental noise, but not physiological signals from the patient;

engaging a third piezoelectric sensor with the patient, at a location remote from the first sensor;

sensing physiological signals and environmental noise with the first and third sensors and environmental noise with the second sensor;

isolating the physiological signals from the environmental noise by subtracting environmental noise sensed by the second sensor from the signals sensed by the first and third sensors;

comparing the physiological signals and environmental noise from the first sensor with the physiological signals and environmental noise from the third sensor to determine locations of the first and third sensors on the patient; and displaying the physiological digital signals.

2. A method for passively monitoring the physiology of a patient in an environment, comprising:

coupling a first sensor with the patient;

coupling a second sensor with the patient at a location remote from the first sensor;

sensing physiological parameters of the patient and conditions of the environment around the patient with both the first and second sensors;

converting the sensed physiological parameters and environment conditions into signals;

correlating the signals from the first and second sensors; and using the correlation to extract signals associated with the physiology of the patient;

calculating an energy spectrum from the signals; and extracting signals associated with the physiology of the patient by identifying peaks in the energy spectrum corresponding to physiological parameters of the patient.

3. The method of claim 2, wherein the first and second sensors comprise passive electromechanical transducers for sensing mechanical activity of the patient's body.

4. The method of claim 3, wherein the sensors comprise piezoelectric sensors.

5. The method of claim 3, wherein each the sensors comprise a polyvinylidene fluoride (PVDF) film.

6. The method of claim 2, wherein each of the first and second sensors comprise a polarized polymer film with piezoelectric properties.

7. The method of claim 6, wherein an interface is disposed between the film and the patient for facilitating transmittal of physiological parameters from the patient to the film.

8. The method of claim 7, wherein the interface is selected from the group consisting of gel, water, air, foam, rubber and plastic.

9. The method of claim 2, wherein the sensing step comprises sensing noise and vibration in the environment around the patient.

10. The method of claim 2, further comprising:

placing a third sensor in a location isolated from the patient for sensing said environmental conditions without said physiological parameters of the patient;

sensing environmental conditions with the third sensor;

converting the sensed environmental conditions into signals; and reducing environmental interference in the signals produced by the first and second sensors by subtracting me signals produced by the third sensor from the signals produced by the first and second sensors.

11. Apparatus suitable for passively monitoring the physiology of a patient in a vibration environment, comprising:

at least two sensors, each of said sensors being capable of passively sensing physiological parameters of a patient at a different location on the patient's body and vibration from an environment around the patient;

a converter communicating with the sensors for converting the sensed physiological parameters and environmental vibration into digital signals; and a processor communicating with the converter for processing the digital signals to extract signals associated with the physiology of the patient by correlating signals between sensors;

wherein the processor further calculates an energy spectrum from the digital signals and extracts signals associated with the physiology of the patient by identifying peaks in the energy spectrum corresponding to selected physiological parameters.

12. The apparatus of claim 11, wherein the sensors comprise electromechanical transducers for sensing mechanical activity of the patient's body and producing electrical signals in response thereto.

13. The apparatus of claim 11, wherein each of the sensors comprise a polarized polymer film with piezoelectric properties.

14. The apparatus of claim 13, wherein each of the sensors comprise a polyvinylidene fluoride (PVDF) film.

15. The apparatus of claim 13, further comprising a pad incorporating the polarized polymer films.

16. The apparatus of claim 11, further comprising a monitor communicating with the processor for displaying the physiological data in real time.

17. The apparatus of claim 16, wherein the monitor is in wireless communication with the processor.

18. The apparatus of claim 11, wherein the processor is in wireless communication with the converter.

19. The apparatus of claim 11, wherein the sensors are disposed along a patient supporting surface.

20. The apparatus of claim 19, wherein the patient supporting surface comprises a medical transport.

21. The apparatus of claim 11, wherein the sensors are disposed in hospital bedding.

22. The apparatus of claim 11, further comprising an environmental sensor isolated from the patient for sensing the environmental vibration without sensing physiological parameters of the patient, said environmental sensor providing output signals corresponding to the environmental vibration, and subtracting the signals produced by the environmental sensor from signals produced by said at least two sensors to reduce vibration interference in the signals produced by said at least two sensors.

23. The apparatus of claim 11, further comprising a pad incorporating the sensors, and an interface within the pad formed of material selected from the group consisting of gel, water, air, foam, rubber and plastic.

24. The apparatus of claim 11, wherein the processor extracts signals associated with cardiac and respiratory activity of the patient.

25. Apparatus for passively monitoring the physiology of a patient, comprising:

a plurality of sensors for sensing mechanical activity at a plurality of different locations on the patient's body;

a converter communicating with the sensors for converting the sensed mechanical activity into a plurality of digital signals; and a processor communicating with the converter for extracting signals due to cardiac activity of the patient by selectively comparing the digital signals from said different locations on the patient's body;

wherein the processor further transforms the digital signals into frequency signals including respiration and heart rate harmonics, and differentiates respiration and heart rate harmonics by selectively comparing signals from said different locations on the patient's body.

26. The apparatus of claim 25, wherein the plurality of sensors comprise a plurality of polarized films with piezoelectric properties.

27. The apparatus of claim 25, wherein the plurality of sensors comprise a plurality of polyvinylidene fluoride (PVDF) films.

28. A method for passively monitoring the physiology of a patient, comprising:
- coupling a plurality of sensors with the patient at different locations on the patient's body;
- sensing mechanical activity of the patient at each of said locations;
- converting the sensed mechanical activity into a plurality of signals;
- extracting signals associated with cardiac activity of the patient by selectively comparing the signals from said different locations on the patient's body; and
- transforming the signals into frequency signals including respiration and heart rate harmonics, and differentiating respiration and heart rate harmonics by selectively comparing signals from different locations on the patient's body.

29. Apparatus for passively monitoring the physiology of a patient, comprising:
- at least two sensors, each sensor comprising a polarized polymer film with piezoelectric properties, for sensing physiological parameters of the patient at different parts of the patient's body;
- a converter communicating with the sensors for converting the sensed physiological parameters into digital signals; and
- a processor communicating with the converter for determining pulse wave velocity in response to the time difference between corresponding signals from the sensors and for converting the pulse wave velocity into signals corresponding to blood pressure data;
- wherein the at least two sensors comprise a first sensor disposed at a first location along a patient supporting surface and a second sensor disposed at a second location along the patient supporting surface remote from the first location.

30. The apparatus of claim 29, wherein the processor converts the pulse wave velocity into signals corresponding to systolic and diastolic blood pressure data.

31. Apparatus for passively monitoring the physiology of a patient, comprising:
- at least two sensors, each sensor comprising a polarized polymer film with piezoelectric properties, for sensing physiological parameters of the patient at different parts of the patient's body;
- a converter communicating with the sensors for converting the sensed physiological parameters into digital signals; and
- a processor communicating with the converter for determining pulse wave travel time in response to the time difference between corresponding signals from the sensors and for converting the pulse wave travel time into signals corresponding to blood pressure data;
- wherein the at least two sensors comprise a first sensor disposed at a first location along a patient supporting surface and a second sensor disposed at a second location along the patient supporting surface remote from the first location.

32. The apparatus of claim 31, wherein the processor converts the pulse wave travel time into signals corresponding to systolic and diastolic blood pressure data.

33. A method for passively monitoring the physiology of a patient, comprising:
- coupling a first sensor with the patient;
- coupling a second sensor with the patient at a location remote from the first sensor;
- sensing physiological signals and environmental noise and vibration with the first and second sensors;
- comparing the physiological signals and environmental noise and vibration from the first sensor with the physiological signals and environmental noise and vibration from the second sensor to determine locations of the first and second sensors on the patient; and
- isolating selected physiological signals from the environmental and noise vibration.

* * * * *

UNITED STATES PATENT AND TRADEMARK OFFICE
CERTIFICATE OF CORRECTION

PATENT NO. : 6,984,207 B1
APPLICATION NO. : 09/662006
DATED : January 10, 2006
INVENTOR(S) : Patrick K. Sullivan et al.

It is certified that error appears in the above-identified patent and that said Letters Patent is hereby corrected as shown below:

Column 6
Line 37, change "FIG. 14 shows schematic" to --FIG. 14 shows a schematic--

Column 10
Lines 58-59, change "environment using P2M"" to --environment using the P2M.--

Column 12
Line 23, change "cushions and seats and seatbacks" to --cushions on seats and seatbacks.--

Column 13
Line 27, delete the word "and"
Line 40, change "wherein each the sensors" to --wherein each of the sensors--
Lines 62-63, change "subtracting me signals" to --subtracting the signals--

Signed and Sealed this

Twenty-first Day of November, 2006

JON W. DUDAS
*Director of the United States Patent and Trademark Office*

UNITED STATES PATENT AND TRADEMARK OFFICE
CERTIFICATE OF CORRECTION

PATENT NO. : 6,984,207 B1  Page 1 of 1
APPLICATION NO. : 09/662006
DATED : January 10, 2006
INVENTOR(S) : Patrick K. Sullivan et al.

It is certified that error appears in the above-identified patent and that said Letters Patent is hereby corrected as shown below:

Title Page
Item [56], References Cited, add the following under the heading "U.S. PATENT DOCUMENTS":

| | | | | |
|---|---|---|---|---|
| -- | 3,742,937 | 7/1973 | Manuel et al. | 128/2.05 |
| | 3,898,981 | 8/1975 | Basham | 128/2 |
| | 4,359,726 | 11/1982 | Lewiner et al. | 340/666 |
| | 4,428,380 | 1/1984 | Wong et al. | 128/715 |
| | 4,628,939 | 12/1986 | Little et al. | 128/696 |
| | 4,734,044 | 3/1988 | Radice | 439/78 |
| | 4,827,763 | 5/1989 | Bourland et al. | 73/172 |
| | 4,926,866 | 5/1990 | Lee | 128/630 |
| | 4,967,760 | 11/1990 | Bennett, Jr. et al. | 128/715 |
| | 5,012,815 | 5/1991 | Bennett, Jr. et al. | 128/715 |
| | 5,036,859 | 8/1991 | Brown | 128/734 |
| | 5,490,516 | 2/1996 | Hutson | 128/696 |
| | 5,590,649 | 1/1997 | Caro et al. | 128/630 |
| | 5,590,650 | 1/1997 | Genova | 128/630 |
| | 5,724,990 | 3/1998 | Ogino | 128/782 |
| | 5,846,206 | 12/1998 | Bader | 600/534 |
| | 5,902,255 | 5/1999 | Ogino | 600/595 |
| | 5,942,979 | 8/1999 | Luppino | 340/576 |
| | 5,989,193 | 11/1999 | Sullivan | 600/534 |
| | 6,047,203 | 4/2000 | Sackner et al. | 600/388 |
| | 6,050,940 | 4/2000 | Braun et al. | 600/300 |
| | 6,146,332 | 11/2000 | Pinsonneault et al. | 600/534 -- |

Signed and Sealed this

Twentieth Day of March, 2007

JON W. DUDAS
*Director of the United States Patent and Trademark Office*

UNITED STATES PATENT AND TRADEMARK OFFICE
CERTIFICATE OF CORRECTION

PATENT NO. : 6,984,207 B1
APPLICATION NO. : 09/662006
DATED : January 10, 2006
INVENTOR(S) : Patrick K. Sullivan et al.

It is certified that error appears in the above-identified patent and that said Letters Patent is hereby corrected as shown below:

Title Page
Item [56], References Cited, add the following under the heading "U.S. PATENT DOCUMENTS":

| | | | | |
|---|---|---|---|---|
| -- | 3,742,937 | 7/1973 | Manuel et al. | 128/2.05 |
| | 3,898,981 | 8/1975 | Basham | 128/2 |
| | 4,359,726 | 11/1982 | Lewiner et al. | 340/666 |
| | 4,428,380 | 1/1984 | Wong et al. | 128/715 |
| | 4,628,939 | 12/1986 | Little et al. | 128/696 |
| | 4,734,044 | 3/1988 | Radice | 439/78 |
| | 4,827,763 | 5/1989 | Bourland et al. | 73/172 |
| | 4,926,866 | 5/1990 | Lee | 128/630 |
| | 4,967,760 | 11/1990 | Bennett, Jr. et al. | 128/715 |
| | 5,012,815 | 5/1991 | Bennett, Jr. et al. | 128/715 |
| | 5,036,859 | 8/1991 | Brown | 128/734 |
| | 5,490,516 | 2/1996 | Hutson | 128/696 |
| | 5,590,649 | 1/1997 | Caro et al. | 128/630 |
| | 5,590,650 | 1/1997 | Genova | 128/630 |
| | 5,724,990 | 3/1998 | Ogino | 128/782 |
| | 5,846,206 | 12/1998 | Bader | 600/534 |
| | 5,902,255 | 5/1999 | Ogino | 600/595 |
| | 5,942,979 | 8/1999 | Luppino | 340/576 |
| | 5,989,193 | 11/1999 | Sullivan | 600/534 |
| | 6,047,203 | 4/2000 | Sackner et al. | 600/388 |
| | 6,050,940 | 4/2000 | Braun et al. | 600/300 |
| | 6,146,332 | 11/2000 | Pinsonneault et al. | 600/534 -- |

UNITED STATES PATENT AND TRADEMARK OFFICE
CERTIFICATE OF CORRECTION

| | |
|---|---|
| PATENT NO. | : 6,984,207 B1 |
| APPLICATION NO. | : 09/662006 |
| DATED | : January 10, 2006 |
| INVENTOR(S) | : Patrick K. Sullivan et al. |

It is certified that error appears in the above-identified patent and that said Letters Patent is hereby corrected as shown below:

Item (56) References Cited, Foreign Patent Documents; add

-- WO   96/36279   11/1996 --.

This certificate supersedes Certificate of Correction issued March 20, 2007.

Signed and Sealed this

Tenth Day of July, 2007

JON W. DUDAS
*Director of the United States Patent and Trademark Office*